United States Patent
Syribeys

(10) Patent No.: US 7,490,967 B2
(45) Date of Patent: Feb. 17, 2009

(54) SOLID STATE LIGHT SOURCE INCLUDING COOLING SYSTEM

(76) Inventor: Philip Syribeys, 4721 Chamblee Dunwoody Rd., Ste 300, Dunwoody, GA (US) 30338

( * ) Notice: Subject to any disclaimer, the term of this patent is extended or adjusted under 35 U.S.C. 154(b) by 144 days.

(21) Appl. No.: 11/419,137

(22) Filed: May 18, 2006

(65) Prior Publication Data

US 2006/0285328 A1    Dec. 21, 2006

Related U.S. Application Data

(60) Provisional application No. 60/690,560, filed on Jun. 15, 2005.

(51) Int. Cl.
*F21V 7/04* (2006.01)
*F21V 5/00* (2006.01)
*A61C 1/00* (2006.01)

(52) U.S. Cl. ............... 362/555; 362/294; 362/573; 362/252; 433/29

(58) Field of Classification Search ......... 362/573, 362/554, 555, 240, 252, 294, 373; 600/2; 607/93; 433/29
See application file for complete search history.

(56) References Cited

U.S. PATENT DOCUMENTS

| | | | | |
|---|---|---|---|---|
| 3,638,013 | A | * | 1/1972 | Keller .................. 362/573 |
| 5,634,711 | A | * | 6/1997 | Kennedy et al. .......... 362/294 |
| 5,908,295 | A | | 6/1999 | Kawata |
| 6,008,264 | A | | 12/1999 | Ostler et al. |
| 6,200,134 | B1 | | 3/2001 | Kovac et al. |
| 6,331,111 | B1 | | 12/2001 | Cao |
| 6,402,347 | B1 | * | 6/2002 | Maas et al. ............... 362/294 |
| 6,439,888 | B1 | | 8/2002 | Boutoussov et al. |
| 6,465,961 | B1 | | 10/2002 | Cao |
| 6,607,384 | B1 | | 8/2003 | Nakanishi |
| 6,611,110 | B1 | | 8/2003 | Fregoso |
| 6,692,250 | B1 | * | 2/2004 | Decaudin et al. ............. 433/29 |
| 6,692,252 | B2 | | 2/2004 | Scott |

(Continued)

FOREIGN PATENT DOCUMENTS

JP          2005-46388 A2     2/2005

(Continued)

OTHER PUBLICATIONS

Dental Compare, DEXcam USB-2, http://www.dentalcompare.com/details/7575/DEXcam-USB-2.html, printed on Jan 3, 2007.

(Continued)

*Primary Examiner*—Ismael Negron
(74) *Attorney, Agent, or Firm*—Law Offices of David M. Lang; David M. Lang

(57) ABSTRACT

An illumination system includes a light source having multiple solid state sources, such as LEDs, and emits light of a color temperature of about 5500° K. The system further includes a flexible optical cable formed by a centrally located optical fiber and five corresponding peripheral optical fibers distributed around the center fiber and a sheath for maintaining the optical fibers in a predetermined spatial relationship, with each of the solid state sources is butt-coupled to one end of a single optical fiber. The solid state sources are thermally coupled to a cooling system, which may include fans or other active cooling elements.

10 Claims, 5 Drawing Sheets

U.S. PATENT DOCUMENTS

| | | | |
|---|---|---|---|
| 6,693,551 | B2 | 2/2004 | Pederson |
| 6,719,558 | B2 | 4/2004 | Cao |
| 6,719,559 | B2 | 4/2004 | Cao |
| 6,755,647 | B2 | 6/2004 | Melikechi et al. |
| 6,755,648 | B2 | 6/2004 | Cao |
| 6,755,649 | B2 | 6/2004 | Cao |
| 6,769,911 | B2 | 8/2004 | Buchalla et al. |
| 6,780,010 | B2 | 8/2004 | Cao |
| 6,783,362 | B2 | 8/2004 | Cao |
| 6,799,967 | B2 | 10/2004 | Cao |
| 6,815,241 | B2 | 11/2004 | Wang |
| 6,824,294 | B2 | 11/2004 | Cao |
| 6,890,175 | B2 | 5/2005 | Fischer et al. |
| 6,910,886 | B2 | 6/2005 | Cao |
| 6,926,524 | B2 | 8/2005 | Cao |
| 6,929,472 | B2 | 8/2005 | Cao |
| 6,932,599 | B1 | 8/2005 | Hartung |
| 6,932,600 | B2 | 8/2005 | Cao |
| 6,934,014 | B1 | 8/2005 | Kleinhuber |
| 6,953,340 | B2 | 10/2005 | Cao |
| 6,954,270 | B2 | 10/2005 | Ostler et al. |
| 6,955,537 | B2 | 10/2005 | Cao |
| 6,969,253 | B2 | 11/2005 | Cao |
| 6,971,875 | B2 | 12/2005 | Cao |
| 6,971,876 | B2 | 12/2005 | Cao |
| 6,974,319 | B2 | 12/2005 | Cao |
| 6,979,193 | B2 | 12/2005 | Cao |
| 6,979,194 | B2 | 12/2005 | Cao |
| 6,981,867 | B2 | 1/2006 | Cao |
| 6,988,890 | B2 | 1/2006 | Cao |
| 6,988,891 | B2 | 1/2006 | Cao |
| 6,989,743 | B2 | 1/2006 | Pederson |
| 6,994,546 | B2 | 2/2006 | Fischer et al. |
| 7,056,116 | B2 | 6/2006 | Scott et al. |
| 7,064,674 | B2 | 6/2006 | Pederson |
| 7,066,732 | B2 | 6/2006 | Cao |
| 7,066,733 | B2 | 6/2006 | Logan et al. |
| 7,074,040 | B2 | 7/2006 | Kanca |
| 7,077,648 | B2 | 7/2006 | Cao |
| 7,086,858 | B2 | 8/2006 | Cao |
| 7,127,163 | B2 | 10/2006 | Lee et al. |
| 7,128,431 | B2* | 10/2006 | Ludewig et al. ............. 362/555 |
| 2002/0172916 | A1* | 11/2002 | Cao ............................ 433/29 |
| 2002/0182563 | A1 | 12/2002 | Boutoussov et al. |
| 2003/0081430 | A1 | 5/2003 | Becker |
| 2004/0033465 | A1* | 2/2004 | Otsuka ........................ 433/29 |
| 2004/0090794 | A1* | 5/2004 | Ollett et al. ................. 362/573 |
| 2004/0141336 | A1 | 7/2004 | West et al. |
| 2004/0165379 | A1* | 8/2004 | Waters ....................... 362/294 |
| 2004/0257808 | A1* | 12/2004 | Bjomson et al. ............ 362/294 |
| 2005/0003322 | A1* | 1/2005 | Logan et al. ................... 433/29 |
| 2005/0116179 | A1* | 6/2005 | Aguirre et al. ........... 250/492.1 |
| 2005/0196720 | A1 | 9/2005 | Ostler et al. |
| 2005/0231974 | A1 | 10/2005 | Marvin |
| 2006/0038192 | A1 | 2/2006 | Williams |
| 2006/0104079 | A1 | 5/2006 | Chen et al. |
| 2006/0154719 | A1 | 7/2006 | Garguilo |
| 2006/0245176 | A1 | 11/2006 | Ostler et al. |
| 2006/0245187 | A1 | 11/2006 | Scott et al. |
| 2007/0297141 | A1* | 12/2007 | Williams .................... 362/373 |

FOREIGN PATENT DOCUMENTS

| | | | |
|---|---|---|---|
| WO | 9916136 | A1 | 4/1999 |
| WO | 0067048 | A2 | 11/2000 |
| WO | 04087594 | A1 | 10/2004 |
| WO | 06034159 | A2 | 3/2006 |
| WO | 06107878 | A2 | 10/2006 |

OTHER PUBLICATIONS

Schweifler, Ken, The New i2 Dryfield Illuminator, http://www.dentalcompare.com/review.asp?rid=18, alleged date Nov. 8, 2005, printed on Jan. 3, 2007.

Chiarulli et a., "Multichannel Optical Interconnections using Imaging Fiber Bundles," OSA Spring Topical Meeting on Optics in Computing (OC'99), OWB3, pp. 112-114, Aspen, CO, Apr. 12-16, 1999.

Fraen Srl, Fraen Fiber Light Injector (FFLI) New Product Announcement, alleged date Jul. 2005, downloaded Dec. 21, 2005.

Fraen Srl, Fraen Fiber Light Injector (FFLI) Data Sheet, alleged date Jul. 22, 2005, downloaded Dec. 21, 2005.

Mitsubishi Rayon Co.,Ltd., Basics of Plastic Optical Fiber, alleged dates: 1997, 2003, downloaded Jan. 31, 2006.

Carlco Technical Plastics, Fibre Coupling LED Optics, alleged date Aug. 19, 2003, downloaded Dec. 21, 2005.

Carlco Technical Plastics, LED Optic Specialist Range, downloaded Dec. 21, 2005.

Doric Lenses Inc., Fiber pigtailed Luxeon™ III Star single LED package, alleged date 2004, downloaded Dec. 21, 2005.

Fraen Srl, FBL Data Sheet, alleged date Nov. 27, 2005, downloaded Dec. 21, 2005.

Fraen Srl, FHS Lens Series Data Sheet, alleged date Jan. 4, 2005, downloaded Dec. 21, 2005.

Fraen Srl, FLP Lens Series Data Sheet, alleged data Jan. 4, 2005, downloaded Dec. 21, 2005.

Doric Lenses Inc., Fiber Pigtailed Luxeon III Star Led Packages, downloaded Dec. 21, 2005.

Lumileds, Technical Datasheet DS46, alleged date Mar. 2005, downloaded Dec. 21, 2005.

Doric et al., Fiber-coupling of LEDs depends on emitter type, alleged date Oct. 2004, downloaded Dec. 21, 2005.

Néron, Fiber Coupling Efficiency Calculation, alleged date Dec. 5, 2005, downloaded Dec. 21, 2005.

Mitsubishi Rayon, Guide Manual for Processing Method for Eska processing Tool THA-300 Set, alleged date Sep. 1, 1999, downloaded Dec. 21, 2005.

Mitsubishi Rayon, Eska Extra Length Cutter THC-300 Operations Manual, alleged date Sep. 1, 1999, downloaded Dec. 21, 2005.

Mitsubishi Rayon, Eska Cable Stripper THS-300 Operations Manual, alleged date Sep. 1, 1999, downloaded Dec. 21, 2005.

Lumileds, The 10 Myths about LEDs, and the Luxeon Difference, downloaded Dec. 21, 2005.

Lumileds, Application Brief AB05, alleged date Aug. 2005, downloaded Dec. 21, 2005.

Lumileds, Application Brief AB07, alleged date Jan. 2005, downloaded Dec. 21, 2005.

Lumileds, Application Brief AB08, alleged date Feb. 2002, downloaded Dec. 21, 2005.

Lumileds, Application Brief AB10, alleged date Jun. 2005, downloaded Dec. 21, 2005.

Lumileds, Application Brief AB11, alleged date Jul. 2005, downloaded Dec. 21, 2005.

Lumileds, Application Brief AB12, alleged date Jan. 2005, downloaded Dec. 21, 2005.

Lumileds, Application Brief AB15, alleged date Apr. 2003, downloaded Dec. 21, 2005.

Lumileds, Application Brief AB17, alleged date Feb. 2005, downloaded Dec. 21, 2005.

Lumileds, Application Brief AB21, alleged date Feb. 2005, downloaded Dec. 21, 2005.

Lumileds, Technical Datasheet DS23, alleged date Apr. 2005, downloaded Dec. 21, 2005.

Lumileds, Technical Datasheet DS23A, alleged date Apr. 2005, downloaded Dec. 21, 2005.

Lumileds, Technical Datasheet DS30; alleged date Sep. 20, 2004, downloaded Dec. 21, 2005.

Lumileds, Technical Datasheet DS40, alleged date Feb. 2004, downloaded Dec. 21, 2005.

Lumileds, Technical Datasheet DS46, alleged date Mar. 2005, downloaded Dec. 21, 2005.

Lumileds, Application Brief AB25, alleged date Feb. 2004, downloaded Dec. 21, 2005.

* cited by examiner

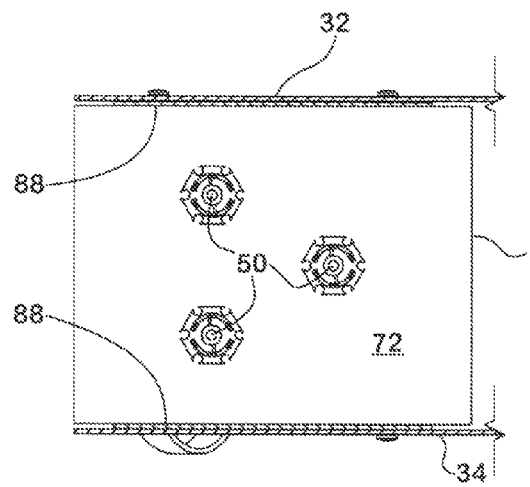
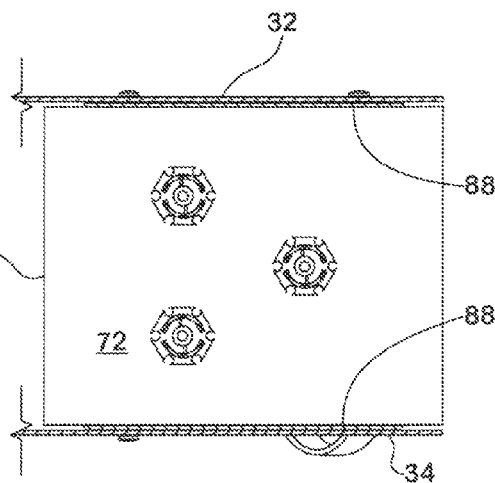
FIG. 6   FIG. 7
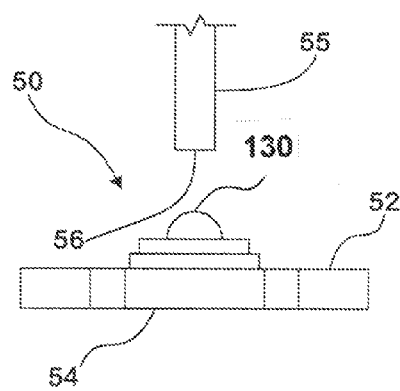
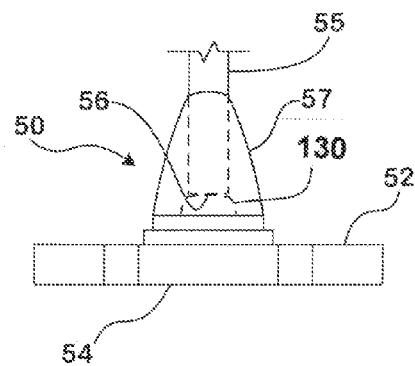
FIG. 8   FIG. 9

SOLID STATE LIGHT SOURCE INCLUDING COOLING SYSTEM

II. CROSS-REFERENCE TO RELATED APPLICATIONS

This application claims the benefit of U.S. Provisional Application No. 60/690,560, filed Jun. 15, 2005.

III. BACKGROUND OF THE INVENTION

This application relates to devices used in healthcare and, more particularly, to a system for illuminating a subject for diagnostic and treatment purposes. More particularly, the application relates to a system for illuminating portions of a dental patient's oral cavity during treatment procedures.

Conventional light sources used during dental procedures rely upon incandescent light sources such as halogen-based light bulbs or arc lamps such as xenon or mercury arc lamps. Light from the light source is transmitted via a fiber optic cable to a light wand or handpiece that may be inserted into a patient's oral cavity during treatment. Light exits a conventional light wand to illuminate the oral cavity during treatment. Typically, the light emanating from conventional sources has a color temperature of about 2800° K to 3500° K, which appears to have a yellowish color. The yellow color of the light emitted from incandescent sources does a poor job of making caries visible to the treating dentist. Caries often appears as a brownish discoloration on the enamel of a patient's tooth. When using an incandescent light source such as a halogen source, the brownish caries appears to be almost the same color as surrounding pale yellow healthy enamel.

Some conventional light sources used in dental procedures incorporate xenon vapor sources that have a much higher color temperature, typically about 6000° K Such sources generate a much whiter light. Xenon sources do a much better job than incandescent sources of making caries easily visible. The brownish color of caries appears much different from surrounding healthy enamel when the caries is illuminated with a xenon source.

However, both incandescent and xenon light sources generate extreme heat. Whenever one of these conventional light sources is coupled to a lighting handpiece via a fiber optic cable, the heat generated by the light source causes the optical fiber in the bundle to deteriorate. Over a relatively short time period, the fiber bundle loses its ability to transmit light resulting in the light emitted from the handpiece growing dimmer. In such systems, manufacturers typically suggest replacing the fiber optic bundle every 12 months. These fiber bundles are expensive and replacing the bundle renders the lighting system and therefore the workstation with which it is associated inoperative during the replacement procedure. The incandescent and xenon sources also consume a great deal of power, typically 250 W or more.

Other lighting handpieces incorporate light sources that are solid state devices such as light emitting diodes (LEDs). Light sources such as these are discussed, for example, in U.S. Pat. No. 5,908,295, which is incorporated in its entirety by this reference. However, these LED sources are typically placed in the handpiece. Moreover, only one LED is used as a light source. One LED alone, when connected to a light wand using an optical fiber, does not produce sufficient light to illuminate satisfactorily the patient's oral cavity.

IV. SUMMARY OF THE INVENTION

The lighting system described below includes a light source that is optically linked to a lighting handpiece via a light-transmitting cable. The light source includes a case that encloses one or more light emitting diodes (LEDs), preferably six LEDs, a cooling system, and appropriate power and control circuitry. An example of a commercially available LED that is suitable for use in the lighting system is the LUXEON® brand LED manufactured by Lumileds Lighting U.S., LLC, for example, the LXK2-PW14-V00. Each LED is optically coupled to an optical fiber waveguide, preferably by butt-coupling the LED to the polished end of the optical fiber. The optical fiber may be glass or plastic (e.g., PMMA). However, plastic optical fiber (POF) is preferred for a number of reasons. First, POF is typically more durable than glass fiber. Second, POF is easier to couple to an LED light source because it typically has a larger overall diameter and a larger core diameter than glass fiber. Third, POF can be bent in a smaller radius than glass without substantial transmission loss. Fourth, POF is typically less expensive than glass fiber. Fifth, POF does not transmit infrared energy very efficiently which prevents it from transmitting heat as much as glass fiber.

The LEDs generate considerably less heat than conventional incandescent and vapor light sources. The LEDs are thermally coupled to a cooling system that transfers virtually all the heat generated by the LEDs away from the LEDs and into the surrounding air. The cooling system preferably includes one or more heat sinks and one or more cooling fans to increase the heat flux of the heat sink(s). Because the LEDs generate comparatively little heat and the heat that they do generate is largely dissipated by the cooling system, the temperature of the optical fibers remains low enough to avoid any damage caused over time by exposure to excessive heat. Optical fiber cables, which typically must be replaced quarterly at great expense can last considerably longer due to the cooler temperature of the LED-based light source.

The optical fibers coupled to the LEDs are bundled into a cable that transmits the light produced by the LEDs from the light source to a lightweight lighting handpiece or wand. The optical fibers are packed inside the sheath of an optical cable having a roughly circular cross section. The fibers are packed into the cable in an arrangement selected to minimize packing fraction losses stemming from the spaces between the individual optical fibers. For example, when six LEDs and six corresponding optical fibers are used in the lighting system, one of the optical fibers is approximately centrally positioned about the longitudinal axis of the cable. The remaining five optical fibers are distributed around the perimeter of the centrally located optical fiber. In this arrangement, one group of three LEDs is attached to the substantially planar surface of a first heat sinK The other group of three LEDs is attached to the substantially planar surface of a second heat sinK These contact surfaces of the first and second heat sinks define two planes that are approximately perpendicular to each other. Preferably, the three LEDs in each group are distributed in a triangular pattern on their respective contact surfaces. More preferably, the three centers of each group of LEDs correspond approximately to the vertices of an equilateral triangle.

The light transmitted to the wand emanates from the distal end of the wand through an optical window or lens. The wand preferably includes controls for increasing and decreasing the brightness of the light emanating from the wand and may also include controls for changing the focus of the beam emanating from the wand. The LEDs used in the lighting system emit light at a color temperature of about 5,500° K. When this light shines on a dental patient's teeth, the dental professional can easily identify those portions of a patient's tooth that is infected by caries because the caries appears in a brownish color that is easily distinguished from the pale yellow color of healthy dentin.

The foregoing general description and the following detailed description are exemplary and explanatory only and do not restrict the claims directed to the invention. The accompanying drawings, which are incorporated in and constitute a part of this specification, illustrate one embodiment of the invention and together with the description, serve to explain the principles of the invention.

V. BRIEF DESCRIPTION OF THE DRAWINGS

Figure 2:
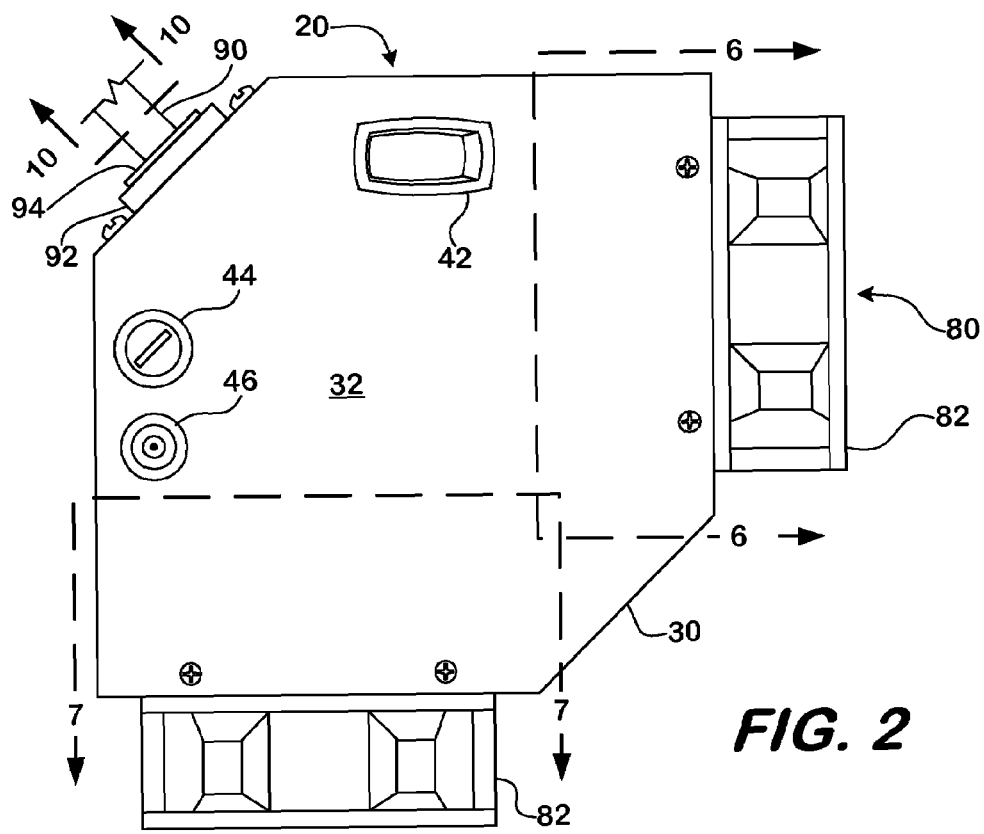
FIG. 2 is a top plan view of an exemplary light source module for the lighting system.

FIG. 6 is a partial cross section view in elevation of a portion of the light source of FIG. 2 as indicated by the line 6-6 on FIG. 2 that illustrates the distribution of three LEDs on the surface of a heat sinK FIG. 7 is a partial cross section view in elevation of a portion of the light source of FIG. 2 as indicated by the line 7-7 on FIG. 2 that illustrates the distribution of three LEDs on the surface of a heat sinK FIG. 8 is a schematic elevation of an LED used in the lighting system.

FIG. 9 is a schematic elevation illustrating an optical waveguide butt coupled to an LED used in the lighting system.

Figure 10:
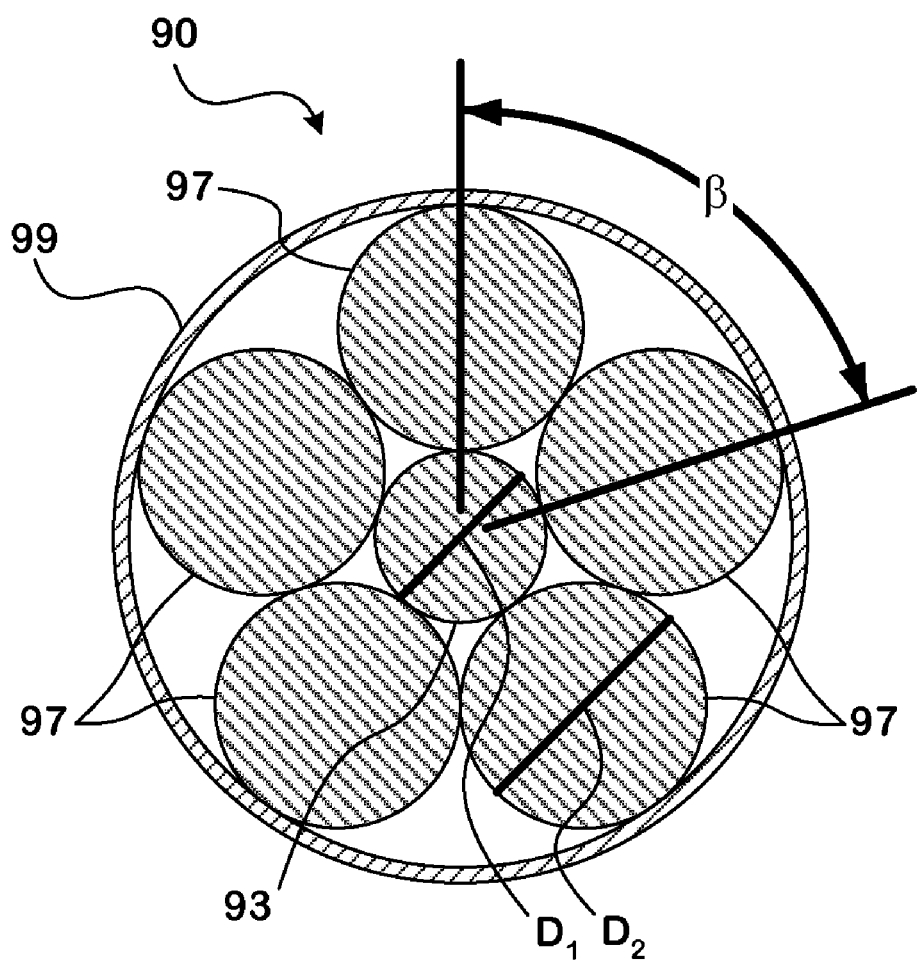

FIG. 10 is a cross section view of an fiber optic cable suitable for use with the light source.

VI. DETAILED DESCRIPTION OF THE INVENTION

This application refers in detail below to an exemplary embodiment of a lighting system for medical procedures, which is illustrated in the accompanying drawings. Wherever possible, the application uses the same reference numbers throughout the drawings to refer to the same or similar items.

Figure 1:
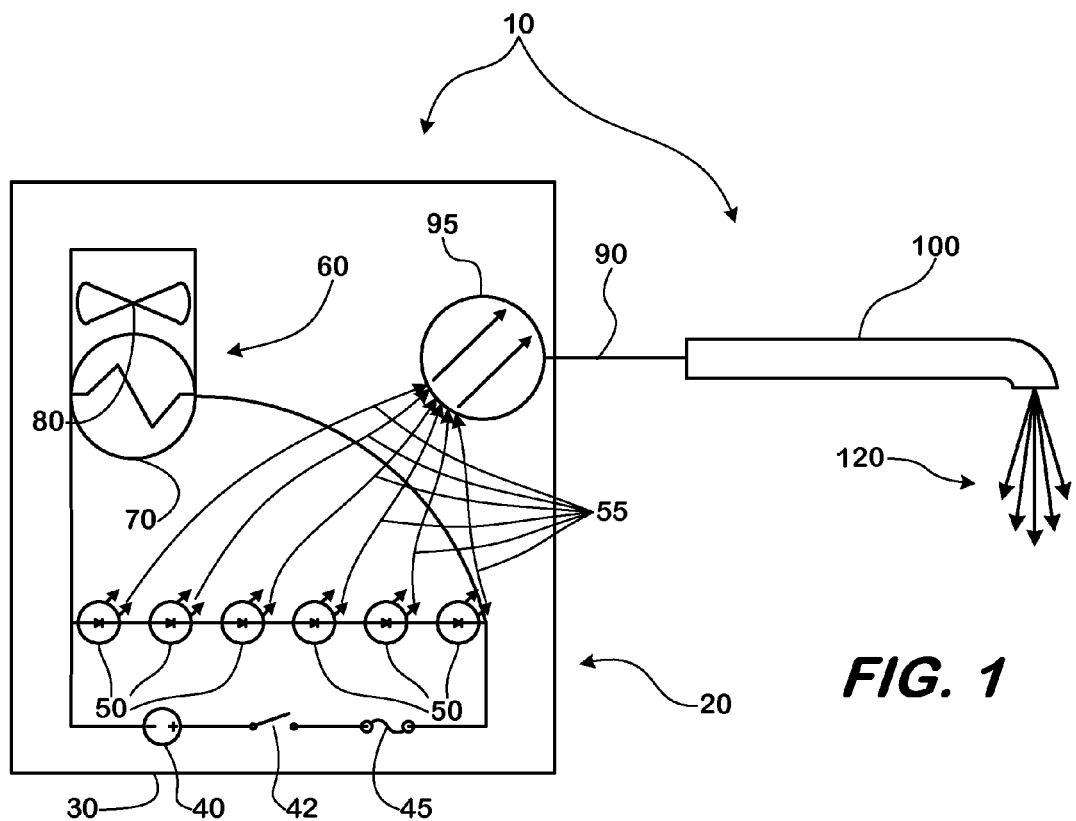
FIG. 1 is a schematic illustration of the main components of a lighting system according to the invention.

The lighting system 10 is illustrated schematically in FIG. 1 with the primary components of the system including a light source 20 having a housing 30, a power source 40, and a group of LEDs 50 with their light output individually coupled to a group of optical fibers 55. A cooling system 60 that carries heat away from the group of LEDs 50 preferably includes a heat sink 70 and a cooling fan 80. The group of optical fibers 55 guide light from the group of LEDs 50 to a light junction 95 of an optical fiber cable 90. The optical fiber cable 90 transmits the light output of the entire group of LEDs 50 to a light wand 100. Light emanates from light wand 100 in a pattern 120.

Figure 1A:
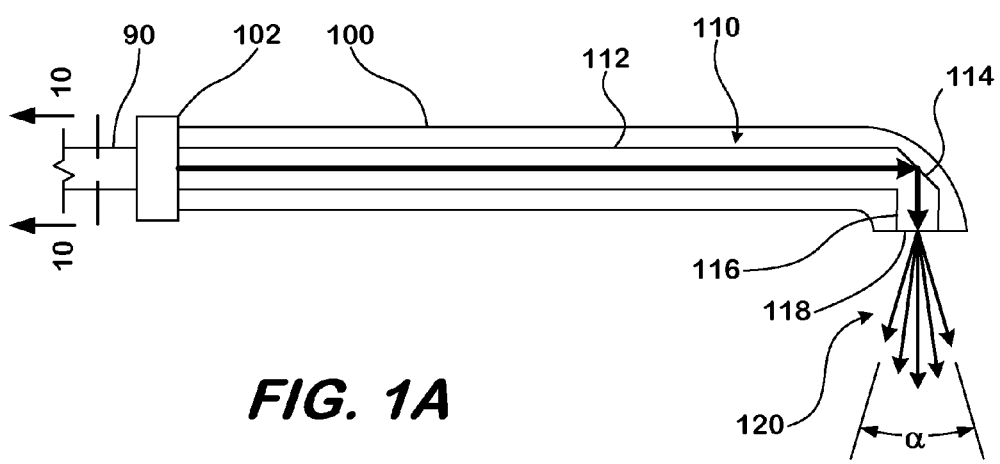
FIG. 1A is a more detailed schematic illustration of the light wand of the lighting system that is illustrated in FIG. 1.

As shown in FIG. 1A, cable 90 connects to wand 100 at connector 102. Light travels inside wand 100 along path 110, which includes a portion 112 along the axis of wand 100, a reflector 114 that redirects the light from its axial direction at an angle to the axis of the wand, and a portion 116 over which the light travels to an opening 118 in the distal end of wand 100. The light emanates from wand 100 through opening 118 in a pattern 120, which is illustrated schematically as a beam that disperses at an angle α. A lens or other type of optic may be positioned along path 110 (e.g., at opening 118) to alter the angle α.

An exemplary embodiment of the light source 20 and some internal components of light source 20 are illustrated in more detail in FIGS. 2-9. The entire light source 20 is shown in FIGS. 2-5. Light source 20 has a housing 30 with top wall 32, bottom wall 34, and side walls 36 and 38. Power switch 42, fuse holder 44, and female power connector 46 are positioned on top wall 32. In the illustrated embodiment, the power supply is in a separate housing from housing 30 and is electrically coupled to the LEDs via a connector that is complementary to power connector 46. The LEDs are protected from an over current condition with a fuse 45 in the electrical path between connector 46 and the LEDs 50. The electrical path between the connector 46 and the LEDs 50 also includes a power switch 42, which in a preferred embodiment may be a rocker switch, mounted in housing 30 to permit easy control of the power to the LEDs 50. Housing 92 of connector 94 is mounted on wall 38 (see FIG. 5). Connector 94 is adapted to mate with a complementary connector on the end of optical cable 95. When light junction 95 is connected to connector 94, light transmitted through optical fibers 55 to light junction 95 is then transmitted into optical cable 90. Optical cable 90 transmits the light to the wand 100, where the light emanates from the distal end of the wand 100.

Cooling system 60 includes heat sinks 70 to which LEDs 50 are thermally connected. The heat sinks are attached to light source 20 by any appropriate means, for example, by a mechanical attachment to housing 30. The cooling system 60 preferably includes cooling fans 80, which in one embodiment may be axial fans, that blow relatively cool air across fins 74 of heat sinks 70 to dramatically improve the efficiency with which LEDs 50 are cooled. In the illustrated embodiment, mounting brackets 88 for the heat sinks 70 and fans 80 are connected to housing 30 with screws that penetrate top wall 32 and bottom wall 34. The fan housing 82 of fan 80 is attached to mounting bracket 88, also using screws. Fan 80 also includes a grating 84 to prevent injury through contact with a spinning fan 86 inside fan housing 82. The same screws that attach mounting bracket 88 to housing 30 also attach heat sinks 70 to the housing. Fans 80 are illustrated as axial fans, but they may be of any type capable of moving sufficient volume of cooling air across the fins 74 of heat sinks 70.

Figure 3:
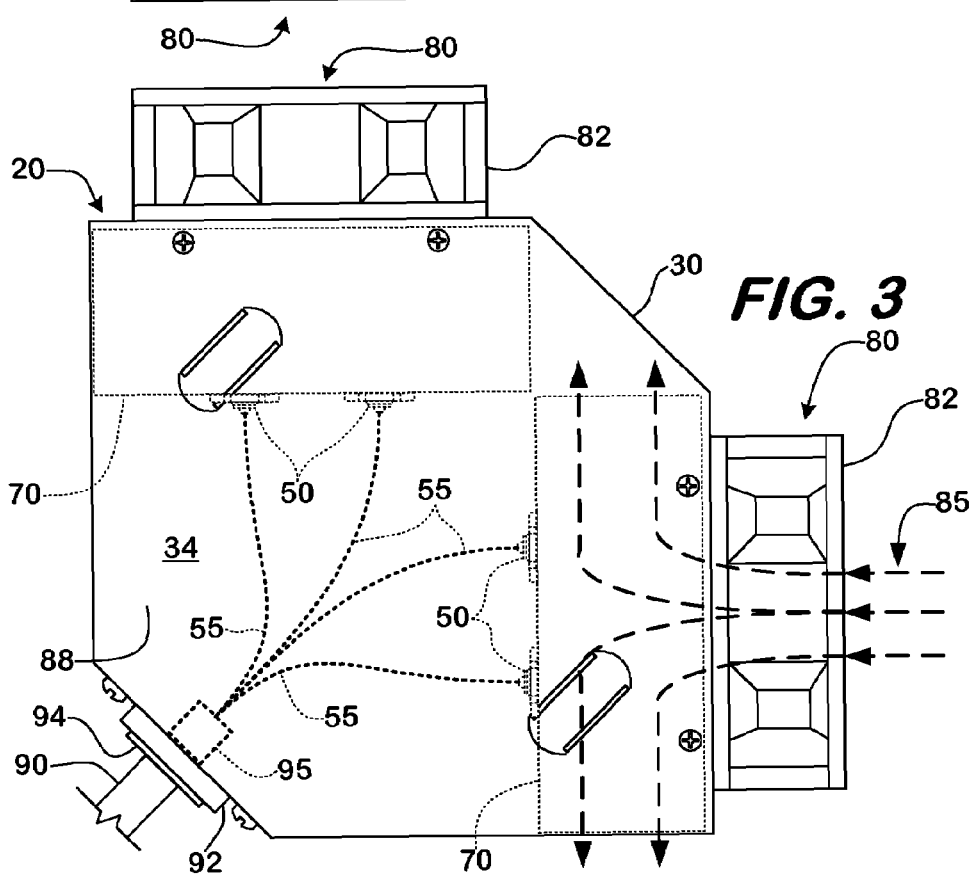
FIG. 3 is a bottom plan view of the light source module of FIG. 2.
Figure 4:
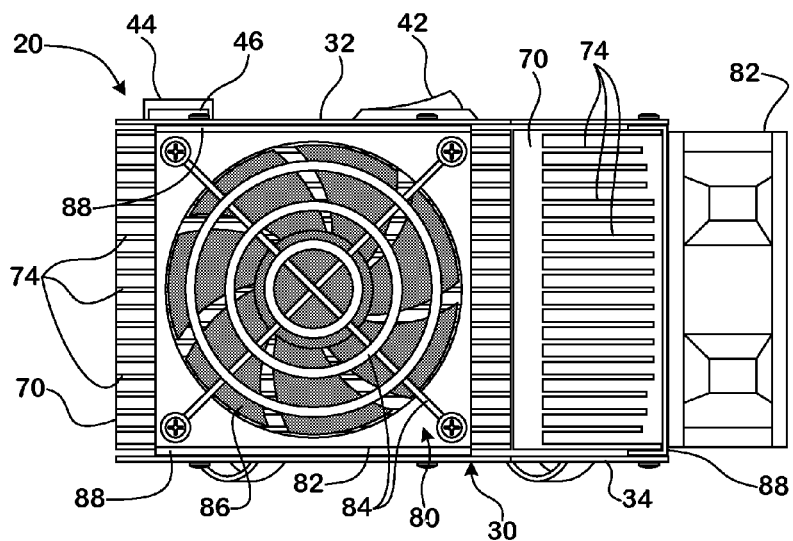
FIG. 4 is a front elevation view of the light source module of FIG. 2.
Figure 5:
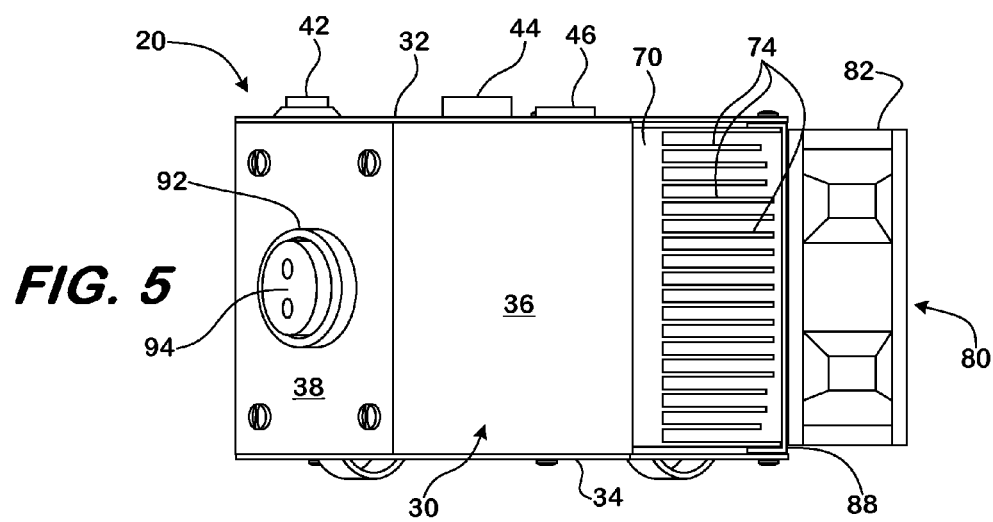
FIG. 5 is a left elevation view of the light source module of FIG. 2.

The positions of heat sinks 70, LEDs 50, optical fibers 55, and fiber junction 95 inside housing 30 are shown by dotted lines in FIG. 3. Because of the mounting arrangement of LEDs 50 on surfaces 72 of heat sinks 70 (see FIGS. 6 and 7), only four LEDs 50 and four optical fibers 55 are shown in FIG. 3. Heat sinks 70 include cooling fins 74 (see FIG. 4) that are spaced apart from each other to permit air to circulate between the fins. Fans 86 are positioned to blow air directly into the spaces between cooling fins 74 in the direction schematically represented by flow lines 85 in FIG. 3.

As illustrated in FIGS. 6 and 7, each of heat sinks 70 have three LEDs 50 mounted on surface 72 with a thermally conductive adhesive. The three LEDs are distributed in a triangular arrangement with their respective centers located approximately at the vertices of an equilateral triangle. The particular arrangement of all six LEDs illustrated in FIGS. 6 and 7 spatially arranges the optical fibers 55 that are coupled to the LEDs to facilitate coupling optical fibers 55 with the optical fiber 93 and optical fibers 97 inside sheath 99 of optical cable 90 (see FIG. 10 for a cross section of optical cable 90).

The preferred method for coupling the LEDs 50 to optical fibers 55 is illustrated in FIGS. 8 and 9, which are detail elevation views. The end face 56 is substantially planar, preferably perpendicular to the longitudinal axis of the fiber, and polished to an optically smooth finish. Additionally, the diameter of optical fiber 55 is preferably at least as large as the longest dimension of the emitter portion of the LED light source (e.g., about 1 mm or more). LED 50 includes a base 52 with a mounting surface 54 at the bottom of the base. Because a pliable lens 130 sits atop the emitter, LED 50 approximates a Lambertian light source. To prevent the LED from overheating, LEDs 50 are mounted on heat sink surface 72 by an adhesive applied to mounting surface 54. The end face 56, preferably a polished face, of optical fiber 55 is pressed against the lens 130 of LED 50 to move the face 56 as close to the emitter as possible without puncturing the lens 130. Face 56 is held in position against the lens 130 by a heat resistant, clear epoxy adhesive 57. When coupled as shown in FIG. 9, approximately 10-20% of the light energy emitted by the LED is captured in and transmitted through the optical fiber 55.

The illustrated embodiment incorporates six LEDs 50 each coupled to an optical fiber 55. One of the six optical fibers 55 is optically joined to an optical fiber 93 that is centrally located in optical fiber cable 90. The other five optical fibers 55 are optically joined to five corresponding optical fibers 97 that are distributed around the perimeter of optical fiber 93 within sheath 99 of the optical fiber cable 90. These six optical junctions between optical fibers 55 and optical fibers 93 and 97 are effected in fiber junction 95. The physical arrangement of optical fiber 93 and five optical fibers 97 is illustrated in the cross section of cable 90 of FIG. 10. The angle β for the illustrated embodiment is 72°. Angle β is defined by two lines that intersect at the center of fiber 93. The first line is defined by the center of optical fiber 93 and the center of one of optical fibers 97. The second line is defined by the center of optical fiber 93 and the center of a second of the optical fibers 97 that is immediately adjacent to the first. To ensure that the five optical fibers 97 are bundled as tightly as possible around optical fiber 93, the diameter D1 of optical fiber 93 is approximately 70% of the diameter D2 of optical fibers 97. When six optical fibers are included in an optical fiber cable, the arrangement illustrated in FIG. 10 maximizes the light-transmitting area in the cross section of the cable.

It will be apparent to those skilled in the art that various modifications and variations can be made in the lighting system for medical procedures and in construction of this lighting system without departing from the scope or spirit of the invention. The embodiment described below is particularly suited for use in dental procedures. However, one could modify the number or color temperature of LEDs used in the light source or the configuration of the light wand and the optics in the wand to suit other medical lighting requirements. One could also include LEDs that emit light of different color temperatures in the light source. Such a system could also include control circuitry allowing the user to alter the light output of these LEDs individually, including turning LEDs off individually. By changing the light output of individual LEDs having different color temperature characteristics, the light wand could emit light exhibiting a variety of color temperatures to suit the user's purposes.

Other embodiments of the lighting system will be apparent to those skilled in the art from their consideration of this description and their use of the system described above. The applicant intends that the specification and examples be considered as exemplary only, with the true scope and spirit of the invention being indicated by the claims appearing below.

What is claimed is:

1. An illumination system, comprising: a housing; a plurality of solid state light sources that are mounted to the housing; a flexible optical cable with a first cable end and a second cable end, said cable having a plurality of optical fibers in which each of the plurality of optical fibers has a first end and a second end and is optically coupled at its first end to one of the plurality of solid state light sources, wherein said cable has a sheath that maintains the plurality of optical fibers in a predetermined spatial relationship to each other along their respective lengths such that the second ends of the plurality of optical fibers lie substantially in a single plane; a cooling system that is thermally coupled to the plurality of solid state light sources, wherein the plurality of solid state light sources comprises at least six light sources, wherein each of the plurality of optical fibers is butt-coupled to one of the plurality of solid state light sources wherein, A. one of the plurality of optical fibers is a central optical fiber and
   B. at least five optical fibers inside the sheath are peripheral optical fibers that are:
      i. positioned substantially parallel to the central fiber and
      ii. distributed evenly around the periphery of the central fiber.

2. The light source of claim 1, wherein a specified angle exists said angle defined by a first line and a second line that intersect at the center of said central fiber, wherein said first line being between the center of the center fiber and the center of a first peripheral fiber, and said second line being between the center of said center fiber and the center of a second peripheral fiber, wherein said first peripheral fiber is immediately adjacent to said second peripheral fiber, wherein said specified angle is 72 degrees.

3. The light source of claim 1, in which each of the peripheral optical fibers is in contact along substantially its entire length inside the sheath with two other peripheral optical fibers and the central optical fiber.

4. The light source of claim 3, comprising at least six light sources and at least six peripheral optical fibers.

5. The light source of Claim 1, wherein the diameter of said central fiber is less than the diameter of said peripheral fibers.

6. The light source of claim 5, wherein the diameter of said central fiber is 70% of the diameter of said peripheral fibers.

7. An illumination system, comprising: a housing; a plurality of solid state light sources that are mounted to the housing; a flexible optical cable with a first cable end and a second cable end, said cable having: a plurality of optical fibers in which each of the plurality of optical fibers has a first end and a second end and is optically coupled at its first end to one of the plurality of solid state light sources, wherein said cable has a sheath that maintains the plurality of optical fibers in a predetermined spatial relationship to each other along their respective lengths such that the second ends of the plurality of optical fibers lie substantially in a single plane; a cooling system that is thermally coupled to the plurality of solid state light sources, wherein the plurality of solid state light sources comprises at least six light sources, wherein each of the plurality of optical fibers is butt-coupled to one of the plurality of solid state light sources, wherein said cooling system comprises a first heat sink having a first mounting surface located in the interior of the housing and a second heat sink having a second mounting surface located in the interior of the housing, wherein at least three of the plurality of light sources are thermally coupled to the first mounting surface and at least three of the plurality of light sources are thermally coupled to the second mounting surface, wherein A. one of the plurality of optical fibers is a central optical fiber and
B. at least five optical fibers inside the sheath are peripheral optical fibers that are:
   i. positioned substantially parallel to the central fiber and
   ii. distributed evenly around the periphery of the central fiber.

8. The light source of claim 7, in which:
A. the first mounting surface is substantially planar,
B. the second mounting surface is substantially planar, and
C. the first mounting surface is oriented substantially perpendicular to the second mounting surface.

9. The light source of claim 8, in which:
A. the first heat sink has a first cooling fins located substantially outside the housing and
B. the second heat sink has a second cooling fins located substantially outside the housing.

10. The light source of claim 9, in which the cooling system further comprises:
A. a first fan that directs air across the first cooling fins, and
B. a second fan that directs air across the second cooling fins.

\* \* \* \* \*